United States Patent [19]

Moser et al.

[11] Patent Number: 4,916,157

[45] Date of Patent: Apr. 10, 1990

[54] ACYLATED NAPHTHYLAMINES AS PLANT FUNGICIDES

[75] Inventors: Hans Moser, Magden, Switzerland; Wolfgang Eckhardt, Lörrach, Fed. Rep. of Germany; Walter Kunz, Oberwil; Adolf Hubele, Magden, both of Switzerland

[73] Assignee: Ciba-Geigy Corporation, Ardsley, N.Y.

[21] Appl. No.: 333,887

[22] Filed: Apr. 3, 1989

Related U.S. Application Data

[60] Continuation of Ser. No. 820,271, Jan. 16, 1986, abandoned, which is a continuation of Ser. No. 430,060, Sep. 30, 1982, abandoned, Ser. No. 430,078, Sep. 30, 1982, abandoned, and Ser. No. 431,522, Sep. 30, 1982, abandoned, said Ser. No. 430,060, Ser. No. 430,078, and Ser. No. 431,522, each is a division of Ser. No. 195,221, Oct. 8, 1980, abandoned, which is a continuation-in-part of Ser. No. 138,066, Apr. 7, 1980, abandoned.

[30] Foreign Application Priority Data

Apr. 10, 1979 [CH] Switzerland ......................... 3404/79

[51] Int. Cl.$^4$ ..................... C07C 103/48; A01N 37/22
[52] U.S. Cl. .................... 514/510; 514/541; 560/10; 560/43
[58] Field of Search ................. 560/10, 43; 514/510, 514/541

[56] References Cited

U.S. PATENT DOCUMENTS

| | | | |
|---|---|---|---|
| 4,151,299 | 4/1979 | Hubele | 560/43 |
| 4,310,463 | 1/1982 | Chan | 549/321 |
| 4,377,587 | 3/1983 | Hubele et al. | 560/43 |

FOREIGN PATENT DOCUMENTS 2008576  6/1979  United Kingdom ................ 549/321

*Primary Examiner*—Richard L. Raymond
*Assistant Examiner*—Patricia L. Morris
*Attorney, Agent, or Firm*—Edward McC. Roberts; Kevin T. Mansfield

[57] ABSTRACT

There are described novel acylated naphthylamines of the formula I defined herein

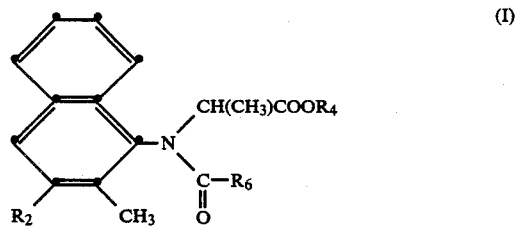

(I)

which have valuable fungicidal properties. They can be used in practice on their own or in the form of compositions for the protection of cultivated plants against fungus infection.

13 Claims, No Drawings

ACYLATED NAPHTHYLAMINES AS PLANT FUNGICIDES

This application is a continuation of application Ser. No. 820,271, filed 1/16/86, now abandoned, which is a continuation of application Ser. Nos. 430,060, 430,078, 430,081 and 431,522, all filed Sept. 30, 1982, now abandoned, all of which are divisions of application Ser. No. 195,221, filed Oct. 8, 1980, now abandoned, which is a continuation-in-part of application Ser. No. 138,066, filed Apr. 7, 1980, now abandoned.

The present invention relates to compounds of the formula I

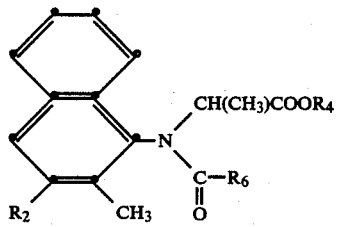

(I)

wherein $R_2$ is hydrogen or methyl; $R_4$ is $C_1$–$C_4$-alkyl, $C_2$–$C_4$-alkenyl, $C_3$–$C_4$-alkynyl or $C_3$–$C_7$-cycloalkyl, each of which is unsubstituted or is substituted by halogen or by $C_1$–$C_2$-alkoxy; and $R_6$ is 2-furyl or 2-tetrahydrofuryl each of which is unsubstituted or is substituted by halogen, or $R_6$ is $\beta$-($C_1$–$C_4$)-alkoxyethyl or the group $CH_2Z$, where $Z$ is one of the groups (a) —X—$R_7$, (b) —NH—N($R_8$)($R_9$), (c) —OSO$_2R_{10}$, (d) —O(CO)$R_{11}$, (e) 1,2-pyrazole or (f) 1,2,4-triazole (1), including the salts and metal complexes thereof, and X is oxygen or sulfur, $R_7$ is a $C_1$–$C_6$-alkyl group optionally substituted by $C_1$–$C_2$-alkoxy, or it is $C_3$–$C_4$-alkenyl or $C_3$–$C_4$-alkynyl, $R_8$ is hydrogen or $C_1$–$C_3$-alkyl, $R_9$ is $C_1$–$C_3$-alkyl or phenyl, $R_{10}$ is $C_1$–$C_4$-alkyl or mono- or di-($C_1$–$C_3$)-alkylamine, and $R_{11}$ is $C_1$–$C_3$-alkyl which is unsubstituted or is substituted by $C_1$–$C_2$-alkoxy.

By alkyl or as alkyl moiety of another substituent are meant, depending on the given number of C atoms, the following groups: methyl, ethyl, propyl, butyl, pentyl and hexyl, as well as isomers thereof, such as iso-propyl, iso-butyl, sec-butyl, tert-butyl and iso-pentyl. Alkenyl is for example allyl or 2-butenyl. Alkynyl is in particular propargyl. $C_3$–$C_7$-cycloalkyl embraces cyclopropyl, cyclobutyl, cyclopentyl, cyclohexyl and cycloheptyl. Halogen is fluorine, chlorine, bromine or iodine.

As metal cations in complexes of compounds of the formula I, there are preferably used those from the main groups II and IV as well as from the subgroups I, II and IV to VIII of the periodic system, for example: Mg, Ca, Ba, Sn, Pb, Cu, Zn, Cd, Cr, Mn, Fe, Co and Ni.

Suitable salt-binding acids for the compounds of the formula (I) are those having good plant tolerance. They include the hydrohalic acids (such as hydrochloric acid and hydrobromic acid), also sulfuric acid, phosphoric acid, nitric acid, mono- and bifunctional carboxylic acids and hydroxycarboxylic acids, for example acetic acid, tartaric acid, citric acid, salicylic acid, lactic acid, 1,5-naphthalene-disulfonic acid, methanesulfonic acid, benzenesulfonic acid, and so forth.

The compounds of the formula I can be produced by a whole series of methods, such as by those given in the following under A-G. In the formulae II to XVIII, the symbols $R_2$ to $R_{11}$ and X have the meanings defined under the formula I, "Hal" is halogen, preferably chlorine or bromine, and M is hydrogen or a metal cation, preferably an alkali metal cation or alkaline-earth metal cation.

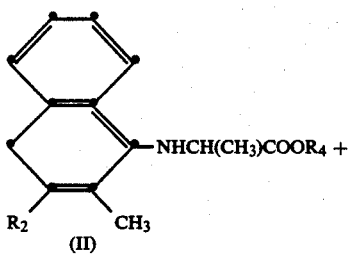

A.

HOOCR$_6$ $\xrightarrow{\text{acylation}}$ (I)

(III)

A reactive derivative of the carboxylic acid of the formula III can advantageously be used, for example the acid halide, acid anhydride or the ester. A suitable acid halide is in particular the acid chloride or acid bromide.

The use of acid-binding agents and condensation agents is in some cases of advantage. Suitable as such are for example: tertiary amines such as trialkylamines (for example triethylamine), pyridine and pyridine bases or inorganic bases, such as the oxides, hydroxides, hydrogen carbonates, carbonates or hydrides of alkali metals and alkaline-earth metals, as well as sodium acetate. The starting product II can also serve as acid-binding agent.

The production process A can also be performed without acid-binding agents; in some cases it is then advisable to pass nitrogen through in order to expel the formed hydrogen halide. In other cases, an addition of dimethylformamide as a reaction catalyst is very advantageous.

B. When $R_6$ is —CH$_2$OSO$_2R_{10}$ or —CH$_2$—O(-CO)$R_{11}$, it is possible, after preliminary acylation of a compound of the formula II with hydroxyacetic acid (or with a derivative thereof) to formula IV, to perform the following variant:

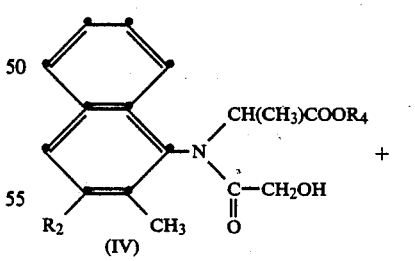

Hal-SO$_2R_{10}$ (V)
or
Hal-CO—$R_{11}$ (VI) $\longrightarrow$ (I)
or
Hal-$R_7$ (VII)

With the reaction variant B, a salt (=alcoholate), particularly an alkali salt of the compound of the formula IV, is advantageously used. This process is carried out if necessary in the presence of an acid-binding agent, such as one of those described under A.

C. Where $R_6$ has a meaning other than $-CH_2NH-N(R_8)(R_9)$, it is possible also to perform the following process variant:

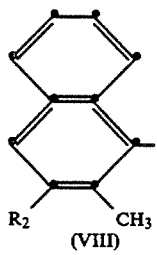

$+ Hal-CH(CH_3)COOR_4 \longrightarrow$ (I)

(VIII)     (IX)

The compound of the formula VIII is in this case firstly converted with butyl-lithium, sodium carbonate or sodium hydride into the corresponding N-alkali salt, or alternatively the process is carried out in the presence of an acid-binding agent in a manner analogous to that of process A, preferably with the addition of a catalytic amount of alkali iodide.

D. When $R_6$ is $-CH_2XR_7$, $-CH_2-O-CO-R_{11}$, $-CH_2NH-N(R_8)(R_9)$ or an azolylmethyl group (azole = 1,2-pyrazole or 1,2,4-triazole), it is possible to perform, after preliminary haloacetylation of a compound of the formula II to formula X, the following variant:

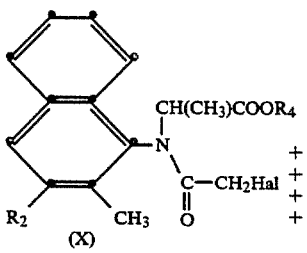

| | |
|---|---|
| + MXR$_7$ | (XI) |
| + MO(CO)R$_{11}$ | (XII) |
| + NH$_2$N(R$_8$)(R$_9$) | (XIII) |
| + M-azole | (XIIIa) |

$\longrightarrow$ (I)

(X)

Where M is hydrogen, the use of a salt-forming agent is appropriate, for example an oxide, hydroxide or hydride of alkali metals or alkaline-earth metals. With use of starting materials of the formula XIII or XIIIa, the final product is obtained as hydrohalide. From this can be obtained using mild bases, at room temperature or at slightly elevated temperature, the free hydrazino or azole base. Alkali carbonates for example are suitable for this purpose.

E. When $R_6$ is $\beta$-($C_1$-$C_4$)-alkoxyethyl:

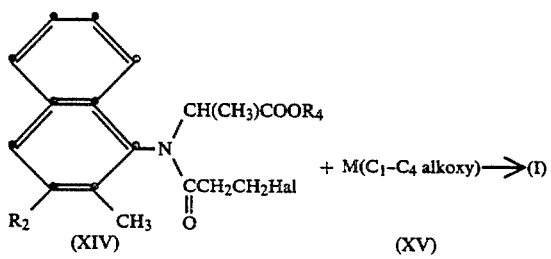

$+ M(C_1-C_4 \text{ alkoxy}) \longrightarrow$ (I)

(XIV)     (XV)

The procedure carried out in this case is analogous to that for the process D.

F. When $R_6$ is $\beta$-($C_1$-$C_4$)-alkoxyethyl:

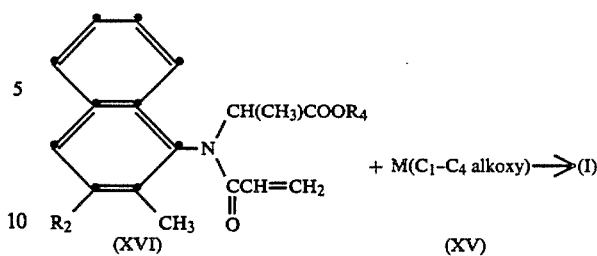

$+ M(C_1-C_4 \text{ alkoxy}) \longrightarrow$ (I)

(XVI)     (XV)

A Michael's reaction is performed in this process with the alcohol or with the alcoholate XV (M=metal atom).

G. The final reaction step carried out can be esterification of the side-chain of the acylamide already formed:

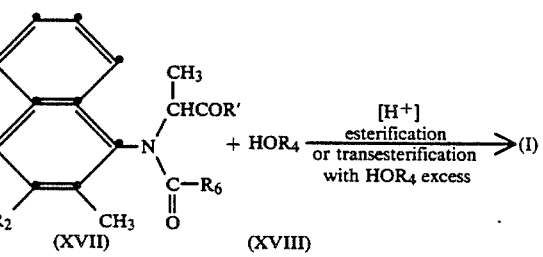

$+ HOR_4 \xrightarrow[\text{or transesterification}]{\substack{[H^+] \\ \text{esterification}}} $ (I)

with HOR$_4$ excess (XVII)     (XVIII)

R' here is either $-OH$ or another alcoholic radical $-OR_4'$ which can be exchanged by customary methods.

If on the other hand R' is a halogen atom, esterification is advantageously performed in the presence of an acid-binding agent.

If R' is OMe, wherein Me is an alkali metal atom, an alkaline-earth metal atom or a lead or silver atom, esterification can also be performed as follows:

$$XVII + Hal'-R_4 \rightarrow (I)$$

wherein Hal' is a halogen atom, preferably chlorine, bromine or iodine.

Solvents which have to be inert to the reactants can be used in all processes. Examples of suitable solvents are: hydrocarbons such as benzene, toluene, xylenes or petroleum ether; halogenated hydrocarbons such as chlorobenzene, methylene chloride, ethylene chloride or chloroform; ethers and ethereal compounds such as dialkyl ether, dioxane or tetrahydrofuran; nitriles such as acetonitrile; N,N-dialkylated amides such as dimethyl formamide; dimethyl sulfoxide, ketones such as methyl ethyl ketone, and mixtures of solvents of this type with each other.

The various processes are included in the subject matter of the present invention.

Some of the starting materials are novel and are also embraced by the invention. They are produced by methods known per se and likewise exhibit fungicidal activity. The compounds of the formula I contain in the ester moiety an asymmetrical carbon atom, and can be split in the customary manner into optical antipodes, for example by fractional crystallisation of the salt formed from a compound of the formula II and an optically active acid, and further reaction of the resulting optical antipode of formula II to an enantiomer of the formula I. Fractional crystallisation of a salt formed from a compound of the formula XVII and an optically active base, and further reaction of the resulting optical antipode of formula XVII to an enantiomer of the formula I is a further possibility for obtaining optical antipodes of the formula I. These exhibit differing microbicidal activities.

Further asymmetrical carbon atoms can occur in the molecule depending on substitution. Owing to the presence of an asymmetric carbon atom in the ester side chain and the steric hindrance about the naphthyl-N<axis, the synthesis of compounds of the formula I usually leads to diastereomeric mixtures. This yields, by separate processing, products having different physical characteristics.

The compounds of the formula I can be used on their own or together with suitable carriers and/or other additives. Suitable carriers and additives can be solid or liquid and they correspond to the substances common in formulation practice, such as natural or regenerated mineral substances, solvents, dispersing agents, wetting agents, adhesives, thickeners, binders and/or fertilisers.

The content of active substance in commercial compositions is between 0.1 and 90%.

For application, the compounds of the formula I can be in the following forms (the weight-percentage figures in brackets signify advantageous amounts of active substance):

solid preparations: dusts and scattering agents (up to 10%), granulates [coated granules, impregnated granules and homogeneous granules] and pellets (1 to 80%);

liquid preparations:
(a) water-dispersible concentrates of active substance: wettable powders and pastes (25 to 90% in the commercial packing, 0.01 to 15% in ready-for-use solutions); emulsion concentrates and solution concentrates (10 to 50%; 0.01 to 15% in ready-for-use solutions);
(b) solutions (0.1 to 20%); aerosols.

Preparations of this type are also embraced by the invention.

In the Belgian Patent Specification No. 871,668 are mentioned in a general form acetamides as fungicides, with individual mention of those compounds which are derived from α-naphthylamine. A typical representative of this series, N-(2-methylnaphthyl)-N-(2-oxo-tetrahydrofuran-3-yl)-N-methoxyacetylamine, is designated in the reproduced tests as being ineffectual. This disclosure gives to a person skilled in the art no indication of the existence of highly effective fungicides within the group of acylated α-naphthylamines of the specific structural pattern of formula I of the present invention. It has been shown surprisingly that within this group novel highly effective plant fungicides are obtained only by combination of specific structural elements, particularly the combination of the groups denoted by $R_6$ with the α-propionic ester side chain and the α-naphthylamine portion. Combinations of this type produce fungicides which are particularly tolerant to plants without causing unpleasant secondary effects. Active substances of the formula I are furthermore characterised by a distinct lasting action and resistence against solar radiation and rainfall.

Accordingly, the present invention relates to the following subgroups of acylated α-naphthylamines:

(Aa) —CO—CH$_2$—X—R$_7$    aliphatic acyl compounds,
(Bb) —CO—CH$_2$—NH—N(R$_8$)(R$_9$)    hydrazinoacetyl derivatives,
(Cc) —CO—CH$_2$—O—SO$_2$R$_{10}$    sulfonyl- and sulfamoyl-acetyl derivatives,
(Dd) —CO—CH$_2$—O—COR$_{11}$    acylated hydroxyacetyl derivatives, (Ee) 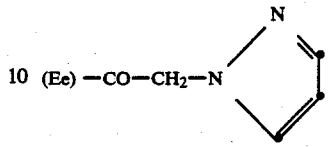    pyrazolyl-acetyl derivatives (and salts and metal complexes thereof), (Ff) triazolyl-acetyl derivatives (and salts and metal complexes thereof), (Gg) optionally halogenated furanoyl and tetrahydrofuranoyl derivatives, and
(Hh) β-alkoxy-propionyl derivatives.

The above subgroups are to be understood together with the remaining portion of the chemical structure of formula I and the respective definitions given for $R_2$ to $R_{11}$ and X.

It has been found that surprisingly compounds having the structure of the formula I exhibit a very favourable microbicidal spectrum for practical requirements for the protection of cultivated plants. Cultivated plants within the scope of the present invention are for example: cereals, maize, rice, vegetables, sugar beet, soya bean, groundnuts, fruit trees and ornamental plants, but particularly grape vines, hops, Cucurbitaceae (cucumbers, pumpkins and melons), Solanaceae, such as potatoes, tobacco and tomatoes, as well as bananas, cocoa and natural rubber plants.

Fungi occurring on plants or on parts of plants (fruit, blossom, foliage, stalks, tubers, roots or rice seedlings) of the said crops and of related crops can be inhibited or destroyed with the active substances of the formula I, and also parts of plants subsequently growing remain preserved from such fungi. The active substances are effective against phytopathogenic fungi belonging to the following classes: Ascomycetes (for example Erysiphaceae, Sclerotinia and Helminthosporiur); Basidiomycetes, such as in particular rust fungi; Rhizoctonia; Fungi imperfecti (for example Moniliales and Piricularia); and particularly against Oomycetes belonging to the Phycomycetes class, such as Phytophthora, Peronospora, Pseudoperonospora, Pythium or Plasmopara. Furthermore, the compounds of the formula I have a systemic action. They can also be used as dressing agents for the treatment of seed (fruit, tubers and grain), and of plant cuttings (for example rice seedlings) to protect them against fungus infections, and also against phytopathogenic fungi occurring in the soil.

The invention thus relates also to the use of the compounds of the formula I for combating phytopathogenic microorganisms.

The following types of substituents and combinations thereof with each other are preferred:
$R_2$ is hydrogen or methyl,
$R_4$ is methyl
$R_6$ is 2-furyl or 2-tetrahydrofuryl or —CH$_2$Z, the meaning of Z being (a) OR$_7$
(b) —NH—N(R$_8$)(R$_9$),
(c) —OSO$_2$R$_{10}$, or
(d) 1,2,4-triazole and salts and metal complexes thereof, wherein R$_7$ is allyl, propargyl or C$_1$–C$_3$-alkyl, R$_8$ and R$_9$ independently of one another are each C$_1$–C$_2$-alkyl, and R$_{10}$ is C$_1$–C$_2$-alkyl or monomethylamine.

Particularly preferred compounds of the formula I are those wherein

R$_2$ is hydrogen or methyl,
R$_4$ is methyl,
R$_6$ is 2-tetrahydrofuryl or —CH$_2$Z, the meaning of Z being:
  (a) —OR$_7$, wherein R$_7$ is methyl, ethyl or propargyl,
  (b) —OSO$_2$R$_{10}$, wherein R$_{10}$ is methyl or monomethylamine, or
  (c) 1,2,4-triazole.

These preferences for R$_2$, R$_4$ and R$_7$ to R$_{10}$ and X also apply to the above indicated subgroups Aa, Bb, Cc, Ff, or Gg, respectively.

In the group of unsaturated aliphatic acyl compounds, the following representatives as fungicides are particularly preferred:
  (A-1) N-(2-methylnaphthyl)-N-(2-propin-1-yloxyacetyl)-alanine-methyl ester [=compound 1.25],
  (A-2) N-(2,3-dimethylnaphthyl)-N-(2-propin-1-yloxyacetyl)-alanine-methyl ester [=compound 1.74].

In the group of saturated aliphatic acyl compounds, the following representatives as fungicides are particularly preferred:
  (B-1) N-(2-methylnaphthyl)-N-(isopropoxyacetyl)-alanine-methyl ester [=compound 1.21],
  (B-2) N-(2,3-dimethylnaphthyl)-N-methoxyacetyl-alanine-methyl ester [=compound 1.67], and
  (B-3) N-(2,3-dimethylnaphthyl)-N-ethoxyacetyl-alanine-methyl ester [=compound 1.75].

In the group of sulfonylated and sulfamoylated acyl compounds, the following representatives as fungicides are particularly preferred:
  (C-1) N-(2-methylnaphthyl)-N-methylsulfonyloxyacetyl-alanine-methyl ester [=compound 1.38],
  (C-2) N-(2-methylnaphthyl)-N-(N'-methylsulfamoyloxyacetyl)-alanine-methyl ester [=compound 1.40].

In the group of triazolylacetyl compounds, the following representative as fungicide is particularly preferred:
  (D-1) N-(2-methylnaphthyl)-N-[1,2,4-triazolyl(1)-acetyl] alanine-methyl ester [compound 1.10].

In the group of furanoyl and tetrahydrofuranoyl compounds, the following representatives as fungicides are particularly preferred:
  (E-1) N-(2-methylnaphthyl)-N-[tetrahydrofuranoyl(2)]alanine-methyl ester [=compound 1.5],
  (E-2) N-(2,3-dimethylnaphthyl)-N-[tetrahydrofuranoyl(2)]alanine-methyl ester [=compound 1.66].

In the group of hydrazinoacetyl compounds, the following representatives as fungicides are particularly preferred:
  (F-1) N-(2-methylnaphthyl)-N-(N'-2-phenylhydrazinoacetyl)-alanine-methyl ester [=compound 1.32],
  (F-2) N-(2-methylnaphthyl)-N-(N',N'-2-dimethylhydrazino acetyl)-alanine-methyl ester [=compound 1.33], and
  (F-3) N-(2,3-dimethylnaphthyl)-N-(N',N'-2-dimethylhydrazinoacetyl)-alanine-methyl ester [- compound 1.70].

The following Examples serve to further illustrate the invention without limiting its scope. Temperature values are given in degrees Centigrade, and percentages and parts relate to weight. Except where otherwise stated, the naming of an active substance of the formula I is to be taken in all cases as meaning the isomeric mixture.

PRODUCTION EXAMPLES

EXAMPLE 1

Production of

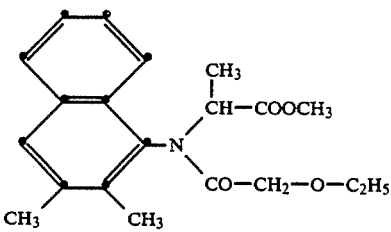

N-(2,3-dimethylnaphthyl)-N-ethoxyacetyl-alanine methyl ester [=compound 1.75].

(a) A mixture consisting of 0.8 g-moles of 2,3-dimethyl-α-naphthylamine, 1.6 g-moles of α-bromo-propionic acid methyl ester and 1.2 g-moles of sodium hydrogen carbonate is heated during 12 hours to 110°, cooled to room temperature and treated with 300 ml of water. The resulting dispersion is then extracted three times with 200 ml of ethylacetate. The organic solution is dried over sodium sulfate and filtered. The solvent is evaporated off. The remaining oil is brought to crystallisation. The crystalline N-2,3-dimethylnaphthyl)-alanine methyl ester is washed with petrol ether (b.p. 40°–60°) and dried; 159.6 g (=77.6% of theoretical amount) of the intermediate product, m.p. 78°–79° C.

(b) During 30 minutes 0.07 g-moles of ethoxyacetyl chloride, dissolved in 20 ml of toluene, and 0.07 g-moles of triethylamine, dissolved in 20 ml of toluene, are dropped at room temperature simultaneously to 0.06 g-moles of N-(2,3-dimethylnaphthyl)-alanine methyl ester, dissolved in 100 ml of toluene. Thereby the temperature rises to 43°. The reaction mixture is then stirred at about 40° during 12 hours. From the resulting yellow suspension the inorganic salt is filtered off and the filtrate is washed with water until neutral. Then the organic phase is dried over sodium sulfate and concentrated by evaporation. The crude oil is purified by column chromatography using silicagel 60 and diethylether as the eluant. After removal of the solvent 18.8 g (=91% of theory) of the final product are obtained in crystallised form, m.p. 96° to 108°.

EXAMPLE 2

Production of

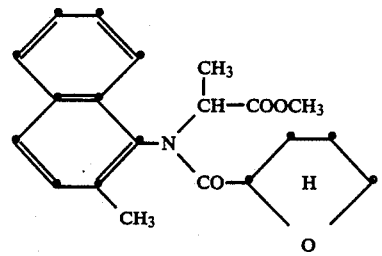
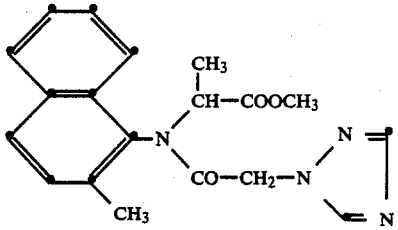

N-(2methylnaphthyl)-N-[tetrahydrofuranoyl(2)]-alanin methyl ester [compound 5].

During 30 min. 0.42 g-moles of tetrahydrofuranoyl chloride are dropped into a solution of 0.37 g-moles of N-(2-methylnaphthyl)-alanine methyl ester (produced by reaction of 2-methylnaphthyl-1-amine and α-bromopropionic acid methyl ester according to the method of Example 1a) in 500 ml of toluene. During the reaction nitrogen is passed through the mixture. The temperature rises from 26° to 46°. Then the reaction mixture is heated to reflux for 4.5 hours. After having it cooled to room temperature the mixture is washed twice with 150 ml of water whereafter the organic phase is dried over sodium sulfate. The solvent is evaporated off. The remaining oil is dissolved in diethyl ether and petrol ether (b.p. 40°-60°) is dropped thereto until the final product crystallises. There are obtained 106 g (=84% of theoretical amount), m.p. 101°-106°.

EXAMPLE 3
Production of

N-(2-methylnaphthyl)-N-[1,2,4-triazolyl(1)-acetyl]-alaninemethyl ester [=compound 10].

15.9 g of N-(2-methylnaphthyl)-N-chloroacetylalaninemethyl ester (produced by reaction of 2-methylnaphthyl-1-amine and α-bromopropionmethyl ester and further reaction of the intermediate with chloroacetyl chloride), 9.1 g of the sodium salt of 1,2,4-triazole and 1 g of KJ in 150 ml of absolute methyl ethyl ketone are refluxed for 17 hours. The reaction mixture is cooled to room temperature, filtered, and concentrated by evaporation. The residue is taken up in 200 ml of ethyl acetate; the solution is then washed twice with 50 ml of water each time, dried with sodium sulfate and concentrated by evaporation. The brown oil remaining is purified through silica gel 60 with acetone as the eluant. The last 4 of 6 fractions are combined and the acetone is evaporated off. The diasterioisomeric mixture of the final product remains as brownish oil, $n_D^{23} = 1.5920$.

The following compounds of the formula I are produced in an analogous manner or by one of the methods described herein.

TABLE 1

| | ($R_2$ = H) | | |
|---|---|---|---|
| Comp. No. | $R_6$ | $R_4$ | Physical constants |
| 1.1 | [tetrahydrofuran-2-yl with O] | —CH₃ | m.p. 128–130° |
| 1.2 | [furanone with Br, O] | —CH₃ | |
| 1.3 | —CH₂OCH₃ | —CH₃ | b.p. 177–180° 0,1 mbar |
| 1.4 | —CH₂OC₂H₅ | —CH₂—CH=CH₂ | |
| 1.5 | [tetrahydrofuran-2-yl with H, O] | —CH₃ | m.p. 101–106° |
| 1.6 | —CH₂OC₂H₅ | —CH₂C≡CH | |
| 1.7 | —CH₂CH₂OCH₃ | —CH₃ | $n_D^{23}$ 1.5673 |
| 1.8 | —CH₂OCH₃ | —CH₂—CH=CH₂ | oil |
| 1.9 | —CH₂OCH₃ | [cyclopropyl] | oil |
| 1.10 | —CH₂N[1,2,4-triazolyl] | —CH₃ | $n_D^{23}$ 1.5920 |

TABLE 1-continued (R₂ = H)

| Comp. No. | R₆ | R₄ | Physical constants |
|---|---|---|---|
| 1.11 | ![cyclic structure with H and O] | —CH₂—CH=CH₂ | |
| 1.12 | —CH₂—N(N=CH—N=) (triazole) | —CH₃ | oil |
| 1.13 | —CH₂O—CH₂CH=CH₂ | —C₃H₇-i | $n_D^{23}$ 1.5571 |
| 1.14 | —CH₂OC₂H₄—OC₂H₅ | —CH₃ | $n_D^{21}$ 1.5562 |
| 1.15 | —CH₂N(triazole)·½CuCl₂ | —CH₃ | m.p. >280° |
| 1.16 | —CH₂OC₂H₅ | —CH₂CH₂OCH₃ | |
| 1.17 | —CH₂N(triazole)·½H₂SO₄ | —CH₃ | m.p. >280° |
| 1.18 | —CH₂OCH₃ | —CH₂—C≡CH | |
| 1.19 | —CH₂OC₂H₅ | —CH₃ | |
| 1.20 | —CH₂OCH₃ | —CH₂CH₂OCH₃ | oil |
| 1.21 | —CH₂OC₃H₇-i | —CH₃ | oil |
| 1.22 | —CH₂OCH₂—CH=CH₂ | —CH₃ | $n_D^{23}$ 1.5700 |
| 1.23 | —CH₂OCH₃ | —CH=CH₂ | |
| 1.24 | —CH₂OCH₃ | —C₄H₉ sek. | |
| 1.25 | —CH₂OCH₂C≡CH | —CH₃ | $n_D^{23}$ 1.5764 |
| 1.26 | —CH₂SCH₃ | —CH₃ | oil |
| 1.27 | ![cyclic structure with H and O] | —CH₂CH₂Cl | oil |
| 1.28 | —CH₂SC₂H₅ | —CH₃ | oil |
| 1.29 | —CH₂N(triazole) | —CH₂CH₂OCH₃ | m.p. 130–145° |
| 1.30 | —CH₂OCH(CH₃)C₂H₅) | —CH₃ | $n_D^{23}$ 1.5532 |
| 1.31 | —CH₂OCH₃ | —CH₂CH₂Cl | |
| 1.32 | —CH₂—NH—NH—(phenyl) | —CH₃ | oil |
| 1.33 | —CH₂—NH—N(CH₃)₂ | CH₃ | oil |
| 1.34 | —CH₂OCH₂C≡CH | —C₃H₇-i | $n_D^{23}$ 1.5615 |
| 1.35 | —CH₂OC₂H₅ | —CH₂CH₂Cl | |
| 1.36 | —CH₂—OSO₂N(CH₃)₂ | —CH₃ | |
| 1.37 | ![cyclic structure with O] | —CH₂CH₂OCH₃ | m.p. 136–143° |
| 1.38 | —CH₂—OSO₂CH₃ | —CH₃ | m.p. 158–166° |

TABLE 1-continued ($R_2 = H$)

| Comp. No. | $R_6$ | $R_4$ | Physical constants |
|---|---|---|---|
| 1.39 | 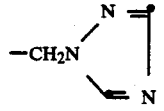 —CH$_2$N(N=•)(•=N) | —C$_3$H$_7$-n | oil |
| 1.40 | —CH$_2$—OSO$_2$NHCH$_3$ | —CH$_3$ | m.p. 141–153° |
| 1.41 | —CH$_2$—O—COCH$_3$ | —C$_3$H$_7$-i | m.p. 169–171° |
| 1.42 | —CH$_2$—OC(=O)CH$_3$ | —CH$_3$ | $n_D^{23}$ 1.5676 |
| 1.43 | —CH$_2$—OC(=O)CH$_2$OCH$_3$ | —CH$_3$ | oil |
| 1.44 | —CH$_2$—CH$_2$OCH$_3$ | —C$_3$H$_7$-i | m.p. 118–130° |
| 1.45 | 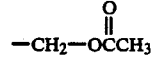 | —CH$_2$CH$_2$OCH$_3$ | m.p. 108–114° |
| 1.46 | —CH$_2$O—SO$_2$NHC$_2$H$_5$ | CH$_3$ | m.p. 132–134° |
| 1.47 | —CH$_2$OCH$_3$ | —C$_3$H$_7$-n | |
| 1.48 | —CH$_2$OCH$_3$ | 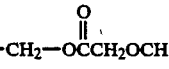 | |
| 1.49 | 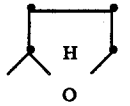 | —C$_2$H$_5$ | m.p. 96–105° |
| 1.50 | —CH$_2$OC$_2$H$_5$ | —CH=CH$_2$ | |
| 1.51 | 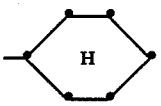 —CH$_2$N(N=•)(•=N) | —C$_2$H$_5$ | oil |
| 1.52 | 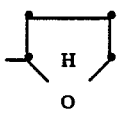 | —C$_3$H$_7$-n | |
| 1.53 | —CH$_2$OC$_2$H$_4$OCH$_3$ | —CH$_3$ | $n_D^{23}$ 1.5603 |
| 1.54 | —CH$_2$OCH$_3$ | —C$_2$H$_5$ | |
| 1.55 | —CH$_2$OCH(CH$_3$)C$_2$H$_5$ | —C$_3$H$_7$-i | $n_D^{22}$ 1.5435 |
| 1.56 | —CH$_2$—OSO$_2$CH$_3$ | —C$_3$H$_7$-i | m.p. 160–168° |
| 1.57 | —CH$_2$NHN(CH$_3$)$_2$ | —C$_3$H$_7$-i | oil |
| 1.58 | —CH$_2$OC$_2$H$_5$ | —C$_3$H$_7$-i | b.p. 188–190°/ 0.1 mbar |
| 1.59 | —CH$_2$O—C$_2$H$_4$—OCH$_3$ | —C$_3$H$_7$-i | $n_D^{22,5}$ 1,5512 |
| 1.60 | —CH$_2$OCH$_3$ | —C$_3$H$_7$-i | m.p. 102–115° |
| 1.61 | —CH$_2$NHNH—C$_6$H$_5$ | —C$_3$H$_7$-i | oil |
| 1.62 | 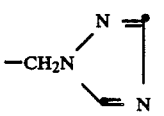 —CH$_2$—N(N=•)(•=N) | —C$_3$H$_7$-i | m.p. 155–162° |
| 1.63 | 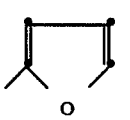 | —C$_3$H$_7$-i | $n_D^{23}$ 1.5901 |

TABLE 1-continued (R$_2$ = H)

| Comp. No. | R$_6$ | R$_4$ | Physical constants |
|---|---|---|---|
| 1.64 | 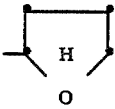 | —C$_3$H$_7$-i | n$_D^{23}$ 1.5665 |

Also following compounds of the formula I can be produced in an analogous manner.

TABLE 2

(R$_2$ = CH$_3$)

| Comp. No. | R$_6$ | Physical constants |
|---|---|---|
| 1.65 | (cyclic structure with O) | m.p. 133–135° |
| 1.66 | (cyclic structure with H, O) | m.p. 118–124° |
| 1.67 | —CH$_2$OCH$_3$ | m.p. 92–100° |
| 1.68 | —CH$_2$—N (triazole) | m.p. 115–122° |
| 1.69 | —CH$_2$CH$_2$OCH$_3$ | m.p. 98–108° |
| 1.70 | —CH$_2$—NH—N(CH$_3$)$_2$ | oil |
| 1.71 | —CH$_2$—O—SO$_2$CH$_3$ | semisolid |
| 1.72 | —CH$_2$—OSO$_2$NHCH$_3$ | m.p. 162–170° |
| 1.73 | —CH$_2$—O—CO—CH$_3$ | viscous |
| 1.74 | —CH$_2$—O—CH$_2$—C≡CH | m.p. 75–85° |
| 1.75 | —CH$_2$—O—C$_2$H$_5$ | m.p. 96–108° |

FORMULATION EXAMPLES

EXAMPLE 1

Dust: The following substances are used to produce (a) a 5% dust and (b) a 2% dust:
(a)
  5 parts of active substance, and
  95 parts of talcum;
(b)
  2 parts of active substance,
  1 part of highly dispersed silicic acid, and
  97 parts of talcum.

The active substances are mixed and ground with the carriers, and in this form they can be applied by dusting.

EXAMPLE 2

Granulate The following substances are used to produce a 5% granulate:
  5 parts of active substance,
  0.25 part of epoxidised vegetable oil,
  0.25 part of cetyl polyglycol ether,
  3.50 parts of polyethylene glycol, and
  91 parts of kaolin (particle size 0.3–0.8 mm).

The active substance is mixed with epoxidised vegetable oil and dissolved in 6 parts of acetone, and the polyethylene glycol and cetyl polyglycol ether are then added. The solution obtained is sprayed onto kaolin, and the acetone is evaporated off in vacuo. A microgranulate of this type is advantageously used for combating soil fungi.

EXAMPLE 3

Wettable powder: The following constituents are used to produce (a) a 70% wettable powder, (b) a 40% wettable powder, (c) and (d) a 25% wettable powder, and (e) a 10% wettable
(a)
  70 parts of active substance,
  5 parts of sodium dibutylnaphtylsulfonate,
  3 parts of naphthalenesulfonic acid/phenolsulfonic acid/formaldehyde condensate (3:2:1),
  10 parts of kaolin, and
  12 parts of Champagne chalk;
(b)
  40 parts of active substance,
  5 parts of sodium lignin sulfonate,
  1 part of sodium dibutylnaphthylsulfonate, and
  54 parts of silicic acid;
(c)
  25 parts of active substance,
  4.5 parts of calcium lignin sulfonate,
  1.9 parts of Champagne chalk/hydroxyethyl cellulose mixture (1:1),
  1.5 parts of sodium dibutylnaphthylsulfonate,
  19.5 parts of silicic acid,
  19.5 parts of Champagne chalk, and
  28.1 parts of kaolin;
(d)
  25 parts of active substance,
  2.5 parts of isooctylphenoxy-polyoxyethylene-ethanol,
  1.7 parts of Champagne chalk/hydroxyethylcellulose mixture (1:1),
  8.3 parts of sodium aluminium silicate,
  16.5 parts of kieselgur, and
  46 parts of kaolin; and
(e)
  10 parts of active substance,
  3 parts of a mixture of the sodium salts of saturated fatty alcohol sulfates,
  5 parts of naphthalenesulfonic acid/formaldehyde condensate, and
  82 parts of kaolin.

The active substances are intimately mixed in suitable mixers with the additives, and the mixture is then ground in applicable mills and rollers. There are obtained wettable powders which have excellent wetting and suspension properties, which can be diluted with water to give suspensions of the concentration required, and which in this form are particularly suitable for leaf application.

EXAMPLE 4

Emulsifiable concentrate: The following substances are used to produce a 25% emulsifiable concentrate:
- 25 parts of active substance,
- 2.5 parts of epoxidised vegetable oil,
- 10 parts of an alkylarylsulfonate/fatty alcohol polyglycol ether mixture,
- 5 parts of dimethylformamide, and
- 57.5 parts of xylene.

Emulsions of the concentration desired can be prepared from these concentrates by dilution with water, and they are particularly suitable for leaf application.

BIOLOGICAL EXAMPLES

1. Action against *Phytophthora infestans* on tomato plants (a) Residual protective action Three weeks after being sown, tomato plants were sprayed with a spray liquor prepared from wettable powder of the active substance (0.02% and 0.006%, respectively, of active substance). After 24 hours, the treated plants were infested with a sporangia suspension of the fungus. An assessment of fungus infection was made after incubation of the infested plants for 5 days at 20° with 90-100% relative humidity.

(b) Residual curative action

Tomato plants were infested, after three weeks' cultivation, with a sporangia suspension of the fungus. After an incubation time of 22 hours in a moist chamber at 20° with 90-100% relative humidity, the infested plants were dried, and then sprayed with a spray liquor prepared from wettable powder of the active substance (0.02% and 0.006%. respectively, of active substance). After the applied coating had dried, the treated plants were returned to the moist chamber. An assessment of fungus infection was made 5 days after infestation. With an application concentration of 0.02% or of 0.006% (*) in tests (a) and (b), the following compounds reduced fungus infection to 0-5%:

| | | | |
|---|---|---|---|
| 1.1   | 1.26* | 1.44  | 1.63  |
| 1.3   | 1.27  | 1.45* | 1.64* |
| 1.5*  | 1.28  | 1.46* | 1.65* |
| 1.7   | 1.29* | 1.51* | 1.66* |
| 1.10* | 1.31* | 1.53  | 1.67* |
| 1.12* | 1.32  | 1.54  | 1.68* |
| 1.15* | 1.33* | 1.55  | 1.69  |
| 1.16* | 1.34* | 1.56* | 1.70* |
|       | 1.35  |       |       |
| 1.17* | 1.36  | 1.57* | 1.71* |
| 1.19* | 1.37  | 1.58* | 1.72* |
| 1.20* | 1.38* | 1.59  | 1.74* |
| 1.21  | 1.39  | 1.60* | 1.75* |
| 1.22  | 1.40* | 1.61* |       |
| 1.25* | 1.42  | 1.62* |       |

(c) Systemic action

A spray liquor produced from wettable powder of the active substance (0.006% of active substance, relative to the volume of soil) was applied to the surface of the soil of three-week-old tomato plants Care was taken to ensure that the spray liquor did not come into contact with the parts of the plants above the soil. After 48 hours, the treated plants were infested with a sporangia suspension of the fungus. The assessment of fungus infection was made after incubation of the infested plants for 5 days at 20° with 90-100% relative humidity. All the active substances listed with respect to tests (a) and (b) prevented, by virtue of the systemic action of the compounds, occurrence of disease on the plants. The plants displayed a healthy appearance.

2. Action against *Plasmopara viticola* on grape vines

Young grape-vine seedlings in the 4-5-leaf stage were sprayed with a spray liquor produced from wettable powder of the active substance (0.02% of active substance). After 24 hours, the treated plants were infested with a sporangia suspension of the fungus. After an incubation of 6 days at 20° with 95-100% relative humidity, an assessment of fungus infection was made.

The active substances listed in the biological Example 1 and also the active substance No. 1.49 prevented fungus infection either completely or virtually completely (0-5% infection).

3. Action against *Pythium debaryanum* on carrots (a) Action after soil application The fungus was cultivated on a carrot-chips nutrient solution, and was then applied to a soil/sand mixture. The soil infested in this manner was placed into flower pots, and sown with sugar-beet seeds. Immediately after sowing, the test preparations, formulated from wettable powder, were applied as aqueous suspensions to the soil (20 ppm of active substance, relative to the volume of soil). The pots were then left for 2-3 weeks in a greenhouse at 20°. The soil during this time was maintained uniformly moist by careful watering with a watering-can.

(b) Action after dressing application

The fungus was cultivated on a carrot-chips nutrient solution, and was then added to a soil/sand mixture. The soil infested in this manner was placed into soil trays, and sown with sugar-beet seeds which had been dressed with the test preparations formulated as dressing powders (0.06% of active substance). The sown trays were left for 2-3 weeks in a greenhouse at about 20°. The soil was maintained during this period uniformly moist by light watering.

For the evaluation of both tests, the percentage of sugar-beet plants which had emerged and also the proportion of healthy plants and diseased plants were determined.

All of the active substances listed in the preceding biological Examples 1 and 2 exhibited a complete action against Pythium spp. (over 90% of plants emerged). The plants had a healthy appearance.

4 Action against *Cercospora arachidicola* on groundnut plants 10-15 cm high groundnut plants were sprayed with a spray liquor prepared from wettable powder of the active substance (0.02% of active substance), and 48 hours later they were infested with a conidiospore suspension of the fungus. The infested plants were incubated for 72 hours at about 21° with high relative humidity, and were subsequently left in a greenhouse until the typical leaf spots appeared. An assessment of the fungicidal action was made 12 days after infestation and was based on the number and size of the occurring spots.

Compounds proving particularly highly effective against Cercospora infestation were, inter alia, those of the subgroups (a)=aliphatic acyl compounds, (c)=sulfonyl- and sulfamoyl- acetyl derivatives, (e)=pyrazolyl-acetyl derivatives and (f)=triazolyl-acetyl derivatives. Fungus infestation was almost completely prevented with the following compounds (0–10% infestation):

(a) Nos. 1.20,1.21, 1.25, 1.34, 1.60, 1.67, 1.69, 1.75;
(c) Nos. 1.40, 1.46, 1.72;
(e) No. 1.12;
(f) Nos. 1.10, 1.15, 1.17, 1.29, 1.68;

and also with the compound No. 1.70.

What is claimed is:

1. An acylated naphthylamine of the formula

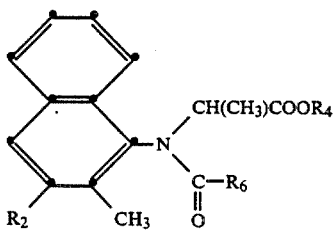

wherein $R_2$ is hydrogen or methyl;

$R_4$ is $C_1$–$C_4$-alkyl, unsubstituted or substituted by halogen or by $C_1$–$C_2$-alkoxy; and $R_6$ is the group $CH_2Z$, wherein Z is -X-$R_7$ wherein X is oxygen or sulfur, and $R_7$ is a $C_1$–$C_6$-alkyl group optionally substituted by $C_1$–$C_2$-alkoxy, or it is a $C_3$–$C_4$-alkenyl or $C_3$–$C_4$-alkynyl group, including the salts and metal complexes thereof.

2. An acylated naphthylamine according to claim 1 wherein $R_4$ is methyl and x is oxygen.

3. An acylated naphthylamine according to claim 2 herein $R_7$ is methyl, ethyl or propargyl.

4. The compound N-(2-methylnaphthyl)-N-methoxyacetyl-alanine methyl ester according to claim 1.

5. The compound N-(2-methylnaphthyl)-N-(2-propyn-1-yloxyacetyl)-alanine methyl ester according to claim 1.

6. The compound N-(2,3-dimethylnaphthyl)-N-(2-propyn-1-yloxyacetyl)-alanine methyl ester according to claim 1.

7. The compound N-(2,3-dimethylnaphthyl)-N-methoxyacetylalanine methyl ester according to claim 1.

8. The compound N-(2,3-dimethylnaphthyl)-N-ethoxyacetylalanine methyl ester according to claim 1.

9. The acylated naphthylamine of claim 1 wherein $R_2$ is hydrogen, $R_4$ is methyl and $R_6$ is —$CH_2OCH_3$.

10. The acylated naphthylamine of claim 1 wherein $R_2$ and $R_4$ are methyl and $R_6$ is —$CH_2OCH_3$.

11. The acylated naphthylamine of claim 1 wherein $R_2$ and $R_4$ are methyl and $R_6$ is —$CH_2OCH_2CH_3$.

12. A plant fungicidal composition comprising an effective amount of a compound according to claim 1 together with a suitable carrier and/or a surface-active additive therefor.

13. A method for combating or preventing fungus infection on plants which comprises applying to the locus to be protected a fungicidally effective compound of a compound of claim 1.

* * * * *